United States Patent [19]
Sword et al.

[11] Patent Number: 6,047,108
[45] Date of Patent: *Apr. 4, 2000

[54] BLOOD WARMING APPARATUS

[75] Inventors: Randall Jay Sword, Danvers; John M. Collins, Ipswich; Ronald J. Forni, Littleton; Michael A. Reed, Chelmsford; Jose Tadeo de Castro, Newton, all of Mass.

[73] Assignee: Baxter International Inc., Deerfield, Ill.

[*] Notice: This patent is subject to a terminal disclaimer.

[21] Appl. No.: 08/724,687

[22] Filed: Oct. 1, 1996

[51] Int. Cl.⁷ ............................ A47J 31/00; A61F 7/00
[52] U.S. Cl. .................... 392/470; 392/466; 219/433; 604/113
[58] Field of Search ................... 392/470, 466, 392/480, 479, 465; 219/432, 433, 435, 535, 534, 497; 604/113–114

[56] References Cited

U.S. PATENT DOCUMENTS

| | | |
|---|---|---|
| 1,514,813 | 11/1924 | Adams . |
| 1,809,077 | 6/1931 | Shuman ................................. 392/479 |
| 1,961,660 | 6/1934 | Fehrmann . |
| 2,342,164 | 2/1944 | Pinkel . |
| 2,424,792 | 7/1947 | Blum . |

(List continued on next page.)

FOREIGN PATENT DOCUMENTS

| | | |
|---|---|---|
| 0309710 | 8/1988 | European Pat. Off. . |
| 444462 | 9/1991 | European Pat. Off. . |
| 4241830 | 6/1994 | Germany . |
| 832538 | 5/1981 | U.S.S.R. . |
| 1578015 | 10/1980 | United Kingdom . |
| 9302722 | 2/1993 | WIPO . |
| 9725080 | 1/1996 | WIPO . |
| 9726029 | 1/1997 | WIPO . |
| 9726032 | 1/1997 | WIPO . |
| 9734445 | 9/1997 | WIPO . |

*Primary Examiner*—Teresa Walberg
*Assistant Examiner*—Thor Campbell
*Attorney, Agent, or Firm*—Jeffrey C. Nichols; Mark J. Buonaiuto; Francis C. Kowalik

[57] ABSTRACT

An apparatus (10) for the controlled heating of fluid comprises a general elongated electrically heating core (16) with an exterior surface (36) formed of a material having a high thermal conductivity and frustoconically shaped to slidingly receive an assembly (14) so that the assembly envelops the surface along at least a portion of the length of the core. The assembly (14) forms a sealed passageway (46) for generally unidirectional sheet-like flow upward along the core (16). A control system (20) selectively operates the heating core (16) so that the fluid, under varying flow rates, is warmed to a desired temperature without overheating, before the fluid flows from the passageway (46).

30 Claims, 6 Drawing Sheets

U.S. PATENT DOCUMENTS

| | | |
|---|---|---|
| 2,576,558 | 11/1951 | Bede . |
| 2,582,871 | 1/1952 | Kintner . |
| 2,636,575 | 4/1953 | Watson . |
| 2,690,653 | 10/1954 | Kleist . |
| 2,766,514 | 10/1956 | Adams . |
| 3,096,426 | 7/1963 | Axelson . |
| 3,171,475 | 3/1965 | Waldman . |
| 3,198,248 | 8/1965 | Stack . |
| 3,293,868 | 12/1966 | Gonzalez . |
| 3,327,776 | 6/1967 | Butt . |
| 3,370,153 | 2/1968 | Fresne et al. . |
| 3,399,536 | 9/1968 | Walz . |
| 3,443,060 | 5/1969 | Smith . |
| 3,475,590 | 10/1969 | Pins . |
| 3,485,245 | 12/1969 | Lahr et al. . |
| 3,551,641 | 12/1970 | Truhan . |
| 3,590,215 | 6/1971 | Anderson et al. . |
| 3,590,917 | 7/1971 | Huber et al. . |
| 3,612,059 | 10/1971 | Ersek . |
| 3,614,385 | 10/1971 | Horstmann . |
| 3,640,283 | 2/1972 | Bhatia et al. . |
| 3,718,182 | 2/1973 | Rossetti . |
| 3,823,457 | 7/1974 | Staas et al. . |
| 3,847,211 | 11/1974 | Fischel et al. . |
| 3,853,479 | 12/1974 | Taloon et al. . |
| 4,019,020 | 4/1977 | Bilbee et al. . |
| 4,038,519 | 7/1977 | Foucras . |
| 4,108,146 | 8/1978 | Golden . |
| 4,167,663 | 9/1979 | Granzow, Jr. et al. . |
| 4,258,784 | 3/1981 | Perry et al. . |
| 4,287,883 | 9/1981 | Kyrias . |
| 4,293,762 | 10/1981 | Ogawa . |
| 4,309,592 | 1/1982 | Le Boeuf . |
| 4,314,143 | 2/1982 | Bilstad et al. . |
| 4,356,383 | 10/1982 | Dahlberg et al. . |
| 4,464,563 | 8/1984 | Jewett . |
| 4,501,952 | 2/1985 | Lehrke . |
| 4,532,414 | 7/1985 | Shah et al. . |
| 4,540,412 | 9/1985 | Van Overloop . |
| 4,574,876 | 3/1986 | Aid . |
| 4,678,460 | 7/1987 | Rosner . |
| 4,680,445 | 7/1987 | Ogawa . |
| 4,707,587 | 11/1987 | Greenblatt . |
| 4,731,072 | 3/1988 | Aid . |
| 4,744,414 | 5/1988 | Schon . |
| 4,759,749 | 7/1988 | Verkaart . |
| 4,782,212 | 11/1988 | Bakke . |
| 4,801,777 | 1/1989 | Auerbach . |
| 4,844,074 | 7/1989 | Kurucz . |
| 4,847,470 | 7/1989 | Bakke . |
| 4,878,537 | 11/1989 | Verkaart . |
| 4,906,816 | 3/1990 | van Leerdam . |
| 4,908,014 | 3/1990 | Kroyer . |
| 4,919,134 | 4/1990 | Streeter . |
| 4,938,279 | 7/1990 | Betker . |
| 4,962,761 | 10/1990 | Golden . |
| 4,966,231 | 10/1990 | Belcher et al. . |
| 4,971,056 | 11/1990 | Seacord . |
| 5,108,372 | 4/1992 | Swenson . |
| 5,125,069 | 6/1992 | O'Boyle . |
| 5,245,693 | 9/1993 | Ford et al. . |
| 5,846,224 | 12/1998 | Sword et al. ............................ 604/113 |

BLOOD WARMING APPARATUS

BACKGROUND OF THE INVENTION

This invention is directed generally to a fluid warming apparatus and, more particularly, to an apparatus for warming parenteral fluid such as whole blood under controlled temperature conditions for transfusion procedures and the like.

Generally, whole blood is stored under refrigerated conditions at temperatures of approximately 4° C. to preserve the quality of the blood over extended periods of time. When the blood is to be infused into a patient, it is necessary that the blood be warmed to approximately 37° C., the temperature of the human body, to avoid possible hypothermia and the attendant risk of ventricular fibrillation and cardiac systole. On the other hand, if the blood temperature is permitted to rise excessively during the warming process, the blood may coagulate or deteriorate.

For many surgical procedures, the quantity of blood which must be warmed for use during the procedure may vary widely. If a quantity of blood is warmed which is sufficient for all foreseen conditions, all of the warmed blood may not be used, resulting in waste of the excess blood since it generally cannot be refrigerated again. Also, for accident victims or other emergency cases, the time required to warm a large quantity of blood for transfusion may become a critical factor.

To heat a large quantity of blood, the blood may be warmed as it flows from a storage assembly to the patient. However, the required flow rate differs among the many surgical conditions and procedures. Indeed during the same surgical procedure, the flow rate of the blood may vary widely. For example, during a procedure a patient may suddenly hemorrhage so that the flow of blood into the patient must be drastically increased. After the hemorrhaging is stopped, the flow of blood may drastically decrease.

It is therefore desirable to be able to controllably warm widely varying flow rates of a fluid, such as blood, with the fluid then delivered to the patient at a generally constant, desired temperature. Additionally if the fluid has an upper temperature limit the heating should be accomplished without overheating and deteriorating the fluid.

Furthermore it is desirable to provide an apparatus which may be operated without undue complexity and have a control system capable of accurately heating the fluid to a desired exit temperature.

It is also desirable to provide an apparatus for warming fluid which incorporates safety features to prevent excess warming due to a malfunction in the control system. In addition, the temperature to which the fluid is being warmed should be readily apparent to operators and other attendant personnel.

Moreover, it is desirable to provide a blood warming device which simplifies any setup and operational supervision in using the device, so that the potential for misuse is reduced.

Due to the danger of the transmission of diseases by injection of a contaminated fluid into the body, it is very important that any fluid warmer not allow contamination of the fluid. Frequently a blood warmer will incorporate a disposable element such as a disposable tube or bag. The element completely contains the fluid as the fluid flows through the warmer.

It is desirable that any disposable element be easy to use with a "nondisposable" element of the warmer. Also if the disposable element is an element of the warmer generally described above, the element should be capable of handling varying flow rates without compromising the performance of the warmer. In addition any disposable element should have a small priming volume to reduce waste.

It is therefore an object of the present invention to provide an improved device for fluid warming. A related object is to provide such an improved device which is particularly adapted to warm, cold parenteral fluids such as whole blood for use during surgical procedures.

It is a further object of the present invention to provide an improved fluid warming device for warming blood and other parenteral fluids to a generally constant temperature over a wide range of flow rates.

It is another object of the present invention to provide an improved fluid warming device which is convenient to operate and requires a minimal amount of operator supervision.

It is a still further object of the present invention to provide an improved fluid warming device which requires a minimum setup time. Furthermore it is desirable that the setup be achieved efficiently and safely.

A still further object of the present invention to provide an improved fluid warming device wherein the element of the device which comes into contact with the fluid during the warming process is disposable.

It is also an object of the present invention to provide a disposable element which is configured to integrate with the operational characteristics of a nondisposable element of the improved warming device. A related object is to provide such a disposable element which can accommodate widely varying flow rates without compromising the operational characteristics of the improved warming device.

It is a still further object of the present invention to provide a disposable element which uses a small priming volume. A related object is that the disposable element facilitate the correct operational attachment to the nondisposable element.

SUMMARY OF THE INVENTION

Accordingly an apparatus for warming a flow of fluid is provided. The apparatus controllably warms the fluid over a wide range or varying flow rates. A preferably disposable assembly of the apparatus accommodates the varying flow rates.

The apparatus includes a heating base having a generally elongated heated mandrel defining an axis. At least a portion of the exterior surface of the mandrel is formed of a material having a high thermal conductivity and shaped to slidingly receive the assembly so that the mandrel heats fluid flowing through the assembly primarily by conduction. The conductive contact principally occurring between the mandrel and assembly.

The assembly includes an outer restraint. Attached to the restraint and disposed along an inner surface of the restraint is a bag. The bag has an inlet and an outlet, each of which are attached to connecting tubing. The bag preferably includes a pair of sidewalls attached to each other to form a sheet-like sealed passageway for the flow of the fluid between the inlet and outlet. The sheet-like passageway extends substantially about the circumference of the surface of the mandrel when the assembly is disposed about the mandrel.

The assembly and mandrel are configured to register the assembly relative to the mandrel so that the passageway through the bag is formed in a desired configuration. More particularly, the inner surface of the outer restraint and an outer surface of the mandrel bracket and constrain the sidewalls to establish a desirably configured, unrestricted sheet-like flow between an inlet and an outlet. The fluid is controllably warmed while flowing through the passageway.

In addition the assembly and mandrel are configured to form a desired flow rate distribution along the mandrel surface. The desired flow rate distribution interacts with the heat distribution along the mandrel surface to promote fluid heating without local hot spots, at which the temperature of the fluid may exceed an upper limit.

The apparatus also includes a system which controls the heat input into the flowing fluid. In dependence on temperature sensor inputs, the control system may vary the heat input to warm the fluid to a desired exit temperature without overheating any portion of the fluid. Preferably, the control system may also control the heat input to compensate for a varying flow rate.

DESCRIPTION OF THE PREFERRED EMBODIMENT

Figures 1, 1A:
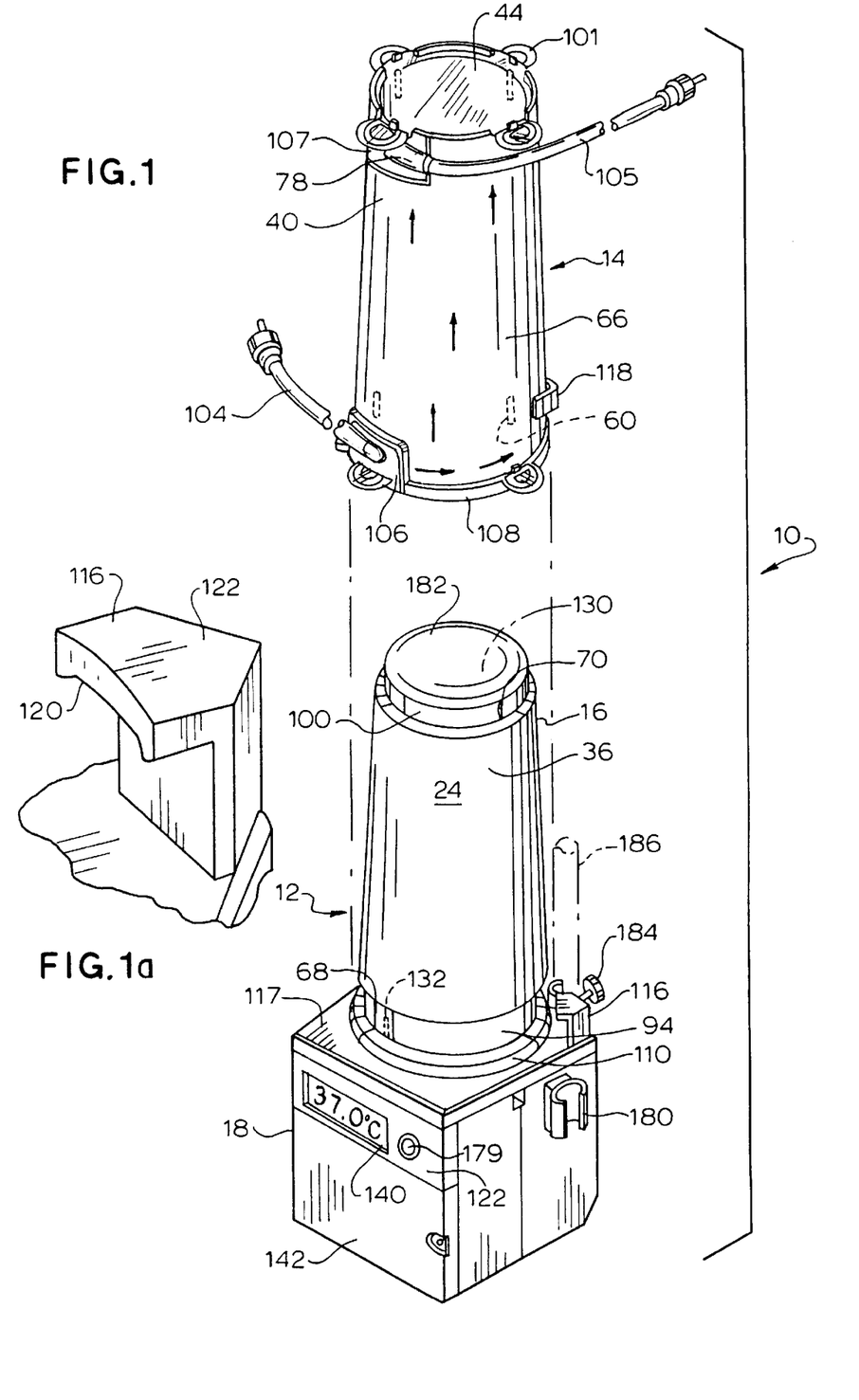
FIG. 1 is a perspective exploded view with parts broken away of a preferred embodiment of the fluid warming apparatus of the present invention.
FIG. 1a is a perspective view of a clamp forming a part of the fluid warming apparatus of FIG. 1.

Referring to FIG. 1, a preferred embodiment of a fluid warmer apparatus of the present invention, particularly configured for the warming of blood, is generally indicated at 10. The warmer 10 includes a heating unit, generally indicated at 12, which controllably warms fluid flowing through a sealed flow path formed by an attached assembly or assembly, generally indicated at 14, which is preferably disposable and removable. The heating unit 12 has a heating core 16 connected to a base 18 which houses a portion of a control system 20, diagramatically represented in FIG. 4.

Figure 2:
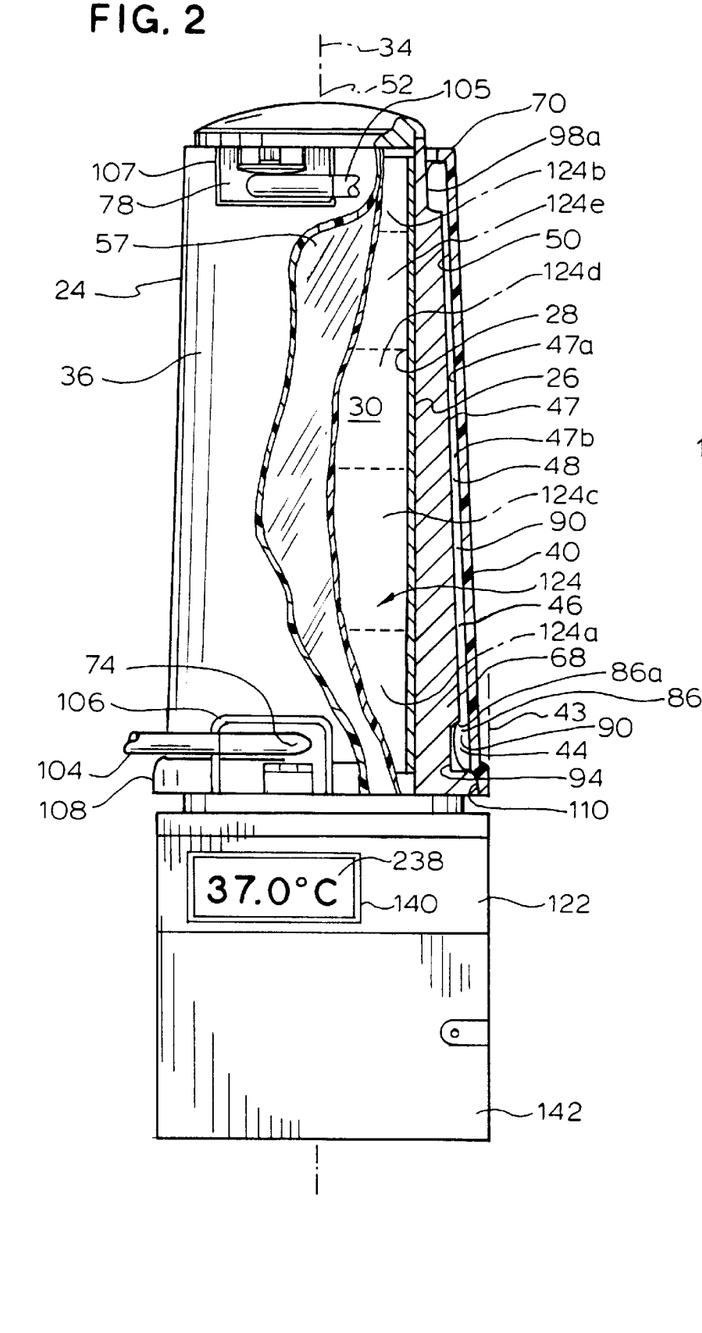
FIG. 2 is a side sectional view of the fluid warming apparatus of FIG. 1.

Referring also to FIG. 2, the heating core 16 has a mandrel 24 composed of a material having high heat conductivity, such as aluminum or the like. Supplying heat to the mandrel 24 is an electrical heater 26 formed as a sheet and in conductive contact with an interior surface 28 of the mandrel. The interior surface 28 is preferably constructed to form a cylindrical cavity 30 extending the height of the mandrel 24 and defining an axis 34 with the heater extending for at least a portion and preferably the majority of the height of the cavity.

An exterior surface 36 of the mandrel 24 is formed to facilitate the removable, enveloping positioning of the disposable assembly 14 about the mandrel. As will be discussed, the proper positioning of the assembly 14 relative to the mandrel 24 is important to obtain optimal performance of the warming apparatus 10. The exterior surface 36 of the mandrel 24 and assembly 14 are formed in complementary frustoconical shapes. Preferably the surface 36 is configured to form a slight slope to a vertical reference 43.

The Attachable Assembly

The assembly 14 includes an exterior restraint 40 and an interior bag or cuff 44 which forms a sealed passageway 46 (FIG. 6) having a general sheet-like configuration, during the flow of fluid through the apparatus 10. It is important to uniquely configure the passageway 46 so that as fluid flows through the warmer apparatus 10 the heat output of the heating unit 12 warms all of the fluid to the desired temperature without exceeding an upper temperature.

For the preferred embodiment of the warmer apparatus 10, a sheet like flow with a generally constant thickness about the heating core is highly desirable. As such, correct relative positioning between the disposable element 14 and mandrel 24 is important. If the restraint is tilted relative to the mandrel 24 the thickness of portions of the passageway 46 are too thin. The flow may be restricted and slow. Similarly the thickness of portions of the passageway on an opposite side of the mandrel are too wide, and the flow may be too great.

It is therefore desirable to configure the restraint 40 and mandrel 24 to establish a boundary 47 for the passageway 46 whereby as fluid flows through the passageway, the passageway is formed with a uniform gap or thickness 48 about a majority of the surface area of the mandrel 24. In one particular desired configuration the passageway 46 is formed with a uniform thickness over a majority of the length of the passageway outward along the mandrel 24. An internal surface 50 of the restraint 40 forms an outer boundary 46a and mirrors the configuration of the exterior surface 36. The exterior surface 36 forms an inner boundary 47b, and the exterior surface 36 and internal surface 50 form the passageway 46 with a uniform thickness when the disposable assembly 14 is juxtaposingly and properly positioned on the mandrel 24. at least a portion and preferably a majority of the length of the passageway.

In the preferred embodiment, a passageway 46 with a thickness of about 0.2 inches is established and such a passageway thickness produces good results. Other thickness will likely produce results sufficient to have the warming apparatus 10 operate within desired parameters.

To ease the effort required for proper positioning of the assembly 14, it is preferred that the assembly 14 be allowed to fit about the mandrel 24 without regard to the relative angular orientation of the assembly and mandrel. In addition, rotation of the assembly relative to the mandrel 24 may be desired. Thus, horizontal cross sections of the internal surface 50 of the restraint 40 and exterior surface 36 of the mandrel 24 are generally circular and concentrically aligned with each other with the centers of the various cross sections defining an axis 52 over a majority of the length of the mandrel 24. Preferably, to facilitate manufacturing, axis 52 and axis 34 are co-linear.

Figure 6:
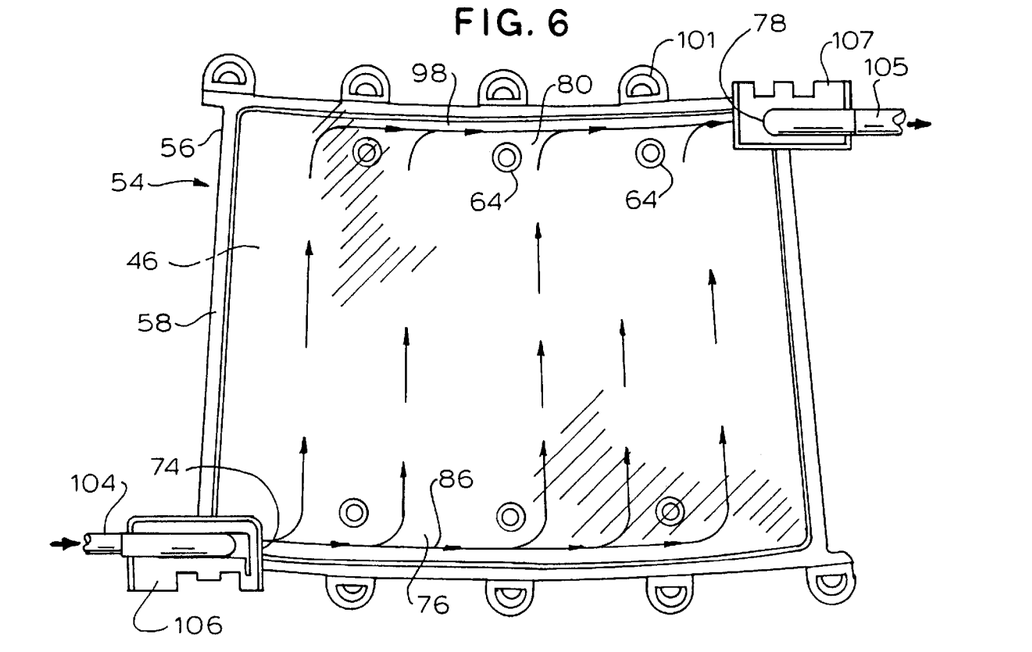
FIG. 6 is a planar view of a cuff forming a part of the apparatus of FIG. 1 and shown in an unfolded position.
Figure 7:
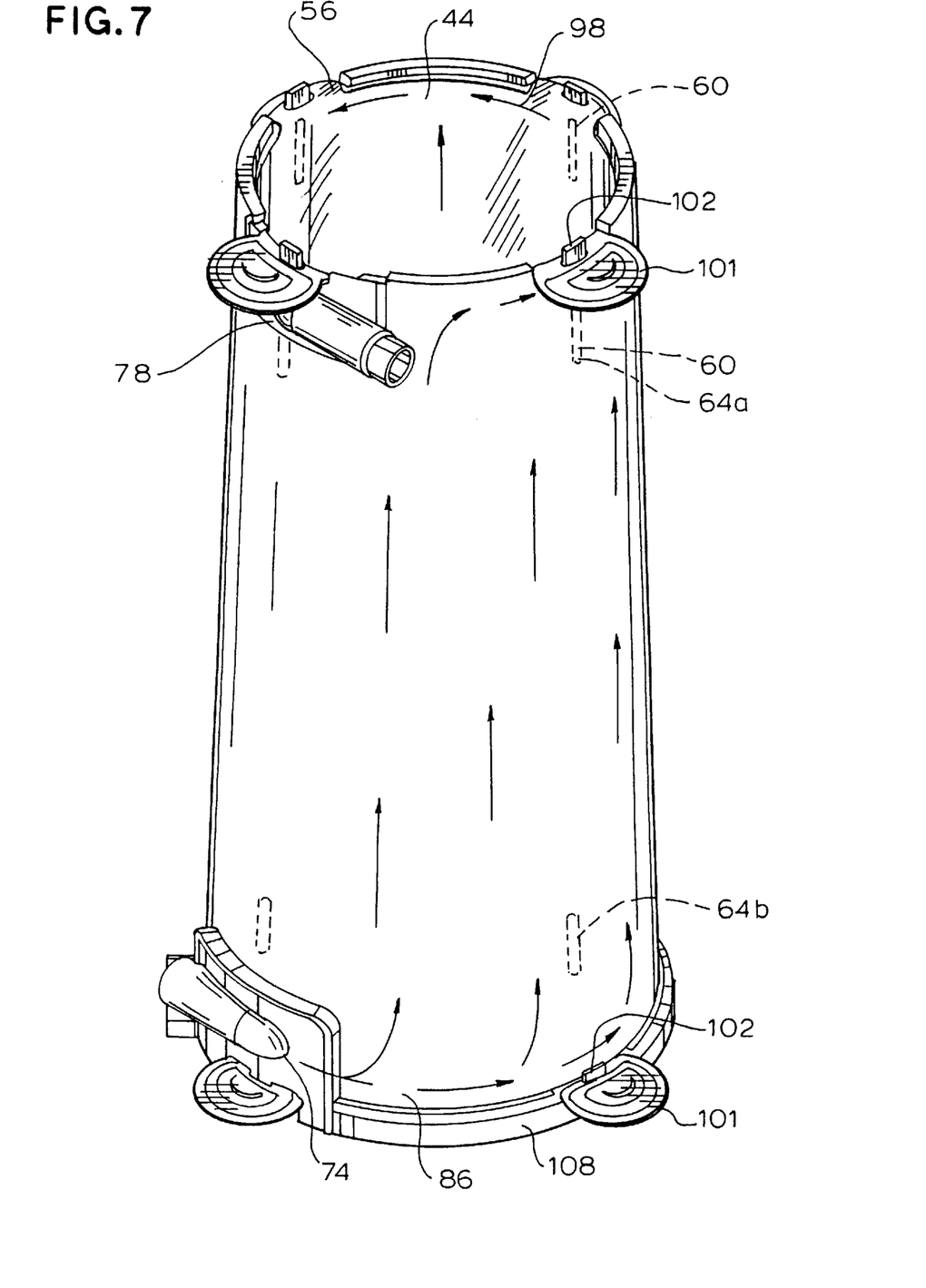
FIG. 7 is a front elevational view of an attachable assembly forming a part of the apparatus of FIG. 1.

Referring to FIGS. 6 and 7, the cuff 44 includes two sheets 54 juxtaposingly positioned and sealingly attached to each other about a peripheral edge 56 to form flexible sidewalls 57 for the sealed sheet-like passageway 46 for the flow of the fluid through the approaches. The cuff 44 is configured and curvingly folded to overlap or place lateral side edges 58 in an aligned abutting relationship and form a frustoconical shape to allow the cuff to be inserted within the restraint 40 and smoothly cover at least a portion of the interior surface 50 of the restraint 40. Preferably, the cuff 44 smoothly and completely covers the interior surface 50 (FIG. 2) along a substantial portion of the height of the restraint 40.

Referring to FIGS. 2 and 6, when fluid under pressure flows through the cuff 44, the fluid forces the sheets 54 against the restraint 40 and mandrel 24 and the passageway 46 assumes the shape of the boundary 47. To register and align the restraint 40 relative to the mandrel 24 to form passageway 46 with the uniform gap 48 axially along and circumferentially around the mandrel 24, a series of standoffs 60 (FIG. 3) are formed to extend inward from the restraint. The standoffs 60 contact the exterior surface 36 of the mandrel 24 to support the assembly in the desired position relative to the mandrel.

As shown particularly in FIG. 7, the 'pinching' of the passageway 46 and disturbance of the sheet like flow by the stand offs 60 is minimal. Preferably for at least a portion and more desirably for over half of the length of the passageway 46 outward along the mandrel 24, the thickness of the passageway 46 within the cuff 44 is uniform circumferentially about the mandrel. Also, the opposing boundary surfaces of the mandrel and restraint 40 are entirely clear of any pinching obstructions over a substantial portion and preferably the majority of the length of the passageway 46. Thus, fluid flowing through the passageway 46 flows in a generally sheet like configuration over a majority of the exterior surface area of the mandrel 24.

In the preferred embodiment, the cuff 44 extends over the standoffs 60. It may be anticipated that the contact between standoffs 60 and the mandrel 24 may damage the cuff 44. Thus, the cuff 44 forms reinforcing dimples 64 which are aligned with the standoffs 60. The dimples 64 are formed so that wear or puncture of the cuff 44 at the dimple does not rupture the passageway 46. The dimples 64 are preferably formed by fusing the sheets 54 together to form a protective seal about the point of contact with the standoff 60.

It is important that the restraint 40 be able to support the cuff 44 so that the flow of fluid under varying pressures and flow rates through the passageway 46 does not cause substantial variations in thickness of the passageway. In addition, the restraint 40 should protect the cuff 44. Therefore, in the preferred embodiment, the restraint 40 is preferably a lightweight rigid shell 66. It is also contemplated that the shell 66 may be pliable or flexible to reduce storage space. It is also envisioned that one of the sidewalls of the cuff 44 may form the restraint 40.

The fluid flowing into the passageway 46 is directed to initially flow about a base 68 of the mandrel 24 and then flow upward in a sheet like configuration along the surface 36 to an upper end 70 of the mandrel. An inlet 74 for the fluid is formed in the cuff 44 at a lower end portion 76 and an outlet 78 is formed at an upper end portion 80.

The mandrel 24 inputs heat, if necessary, to warm the fluid to the desired exit temperature. Especially if the fluid has an upper temperature limit, it is desirable that the fluid flow distribution be generally uniform within the passageway and about the mandrel 24. The restraint 40, cuff 44 and mandrel 24 cooperate so that fluid flowing into the passageway 46 first circumscribes the mandrel 24 before forming the sheet like flow which flows generally uniformly along the mandrel.

Particularly at high flow rates, the width or gap thickness of the passageway may hinder the initial distribution of the fluid about the mandrel 24 when the fluid initially flows into the inlet 74. Therefore it is desirable to form an inlet manifold portion 86 of the passageway 46 which circumscribes the mandrel 24 along a lower edge 88 of the cuff 44. The inlet manifold 86 is preferably formed by forming either the mandrel 24 or restraint 40 or both to form the inlet manifold 86 with a wider gap thickness than the thickness of the passageway along an intermediate portion or section 90 of the passageway 46.

In the preferred embodiment, a radial groove 94 is formed in the mandrel 24 to circumscribe the base 68, and the restraint 40 and groove form a boundary 86a of the inlet manifold 86, as shown particularly in FIG. 1. Alternately the restraint 40 could be configured with an outward extending radial ring portion (not shown). It is also contemplated that both the mandrel 24 and restraint 40 could be configured to form the boundary 86a for manifold 86.

Along similar reasoning, an outlet manifold portion 98 of the passageway is formed to circumscribe the mandrel 24 about the upper end 70 preferably by forming the mandrel with an upper radial groove 100. The groove 100 and restraint 40 form a boundary 98a of the outlet manifold 98. Alternate arrangements, as set forth above, are also contemplated.

To cooperate with the inlet manifold 86, the inlet 74 is formed to direct the fluid along the length of the inlet manifold. Similarly the outlet 78 is formed so that fluid exiting from the passageway 46 flows out in directional alignment with the outlet manifold 98. Therefore the inlet 74 and outlet 78 are formed to direct the fluid tangentially relative to the curved opposing surfaces of the restraint 40 and mandrel 24 and in directional alignment with the corresponding manifolds. As can be seen, it is preferred that the inlet 74 and outlet 78 direct the fluid generally normal to the axis 54 of the assembly.

The inlet 76 is connected to an inlet tube 104, and the tube directs the inflowing fluid in the desired tangential and aligned direction. The peripheral edges 56 of the sheets 54 are sealingly bonded about the tube 104. To provide strain relief, anchor and direct the tube 104 relative to the restraint 40, the assembly 14 includes a bracket 106 which connects to the restraint. The bracket 106 also provides for passage of the tube 104 through the restraint 40 and into the gap 48 in the desired direction.

The outlet 78 is connected to an outlet tube 105 which is aligned with the outlet manifold 98, and fluid flowing along the manifold 98 is directed into the tube. The peripheral edges 56 of the sheets 54 are sealingly bonded about the tube 105. To provide strain relief, anchor and direct the tube 105 relative to the restraint 40, the assembly 14 includes an upper bracket 107 which connects to the restraint. The bracket 107 also provides for passage of the tube 104 through the restraint 40 and into the gap 48 in the desired direction.

The cuff 44 may be formed with a series of outward ears 101 which attach to tabs 102 (formed along or adjacent to the edges of the restraint 40) and maintain the cuff in a layer like configuration along the interior surface 50.

When the assembly 14 is placed on the mandrel 24 and pressurized fluid is flowing through the passageway 46, opposing hydraulic forces are applied by the sheets 54 on the mandrel and assembly. Due to the generally circular horizontal cross section of the restraint 40, the forces on the restraint are directed generally radially outwardly and equally balanced about the circumference of the mandrel 24. The hoop strength of the restraint 40 then counteracts the forces without requiring a latching mechanism or reinforced connecting points between the heating unit 12 and disposable assembly 14.

Oppositely directed hydraulic forces force the sidewall 54 of the cuff 44 into contact with the mandrel 24 to establish good conductive contact between the cuff 44 and mandrel.

Also, to facilitate the proper positioning of the assembly 14 relative to the mandrel 24, a lower apron 108 is fashioned on the shell 44 to abuttingly contact a radial boss 110 on the mandrel 24 and vertically align the shell with the mandrel. It is envisioned that the standoffs 60 principally performs the alignment of the assembly 14 relative to the base 18, but the lower edge contact between apron 108 and boss 110 assists in preventing the assembly from being inadvertently jammed onto the mandrel 24 by the user.

Figure 3:
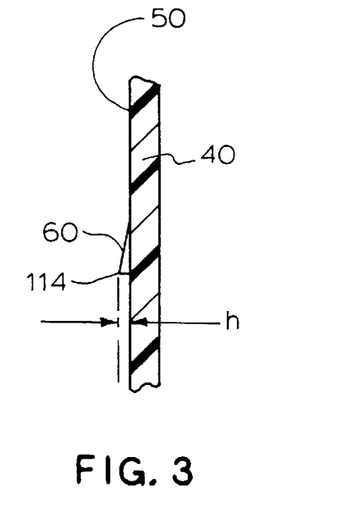
FIG. 3 is an enlarged sectional view of standoff portions of an assembly forming a part of the fluid warming apparatus of FIG. 1.

Referring to FIGS. 3 and 7, the standoffs 60 are preferably integrally formed with the restraint 40, generally elongated and wedge shaped and form a tip 114 which contacts the mandrel 24. The height "h" of the standoff 60 corresponds to the desired thickness of the gap 48 (FIG. 2). The standoffs 60 are selectively placed so that when the restraint 40 is properly positioned relative to the mandrel 24, the standoffs contact the mandrel and establish the gap. Preferably, the standoffs 64 are arranged to form two horizontally aligned sets, an upper set 64a close to an upper end of the mandrel 24, and a lower set 64b close to a lower end of the mandrel. Each of the sets 64a and 64b are preferably equally angularly spaced about the circumference.

Referring to FIGS. 1 and 1a, to lock the assembly 14 on the heating unit 12 and yet allow for removal of the assembly, the heating unit includes a clamp 116 extending upward from an upper surface 117 of the base 18 in close proximity to the mandrel 24. The clamp 116 coordinates with an outward extending ear 118 formed on the lower end of restraint 40. To lock the cup 14 to the unit 12, the disposable assembly 14 is slidingly placed about the mandrel 24 until the lower apron 108 contacts the boss 110 and the standoffs 60 contact the mandrel 24. The cup 14 is then rotated until the ear 118 locks under the clamp 116. Referring to FIG. 1a, to provide an indication of the locking as well as provide a small resistance to unlocking thereby reducing the chance of inadvertent unlocking, a notch 120 is formed along an underside of an upper element 122 of the clamp. The notch 120 is configured to seat the ear 118 when the assembly 14 is properly aligned with and locked to the base 18.

The Heater Unit

Figure 8:
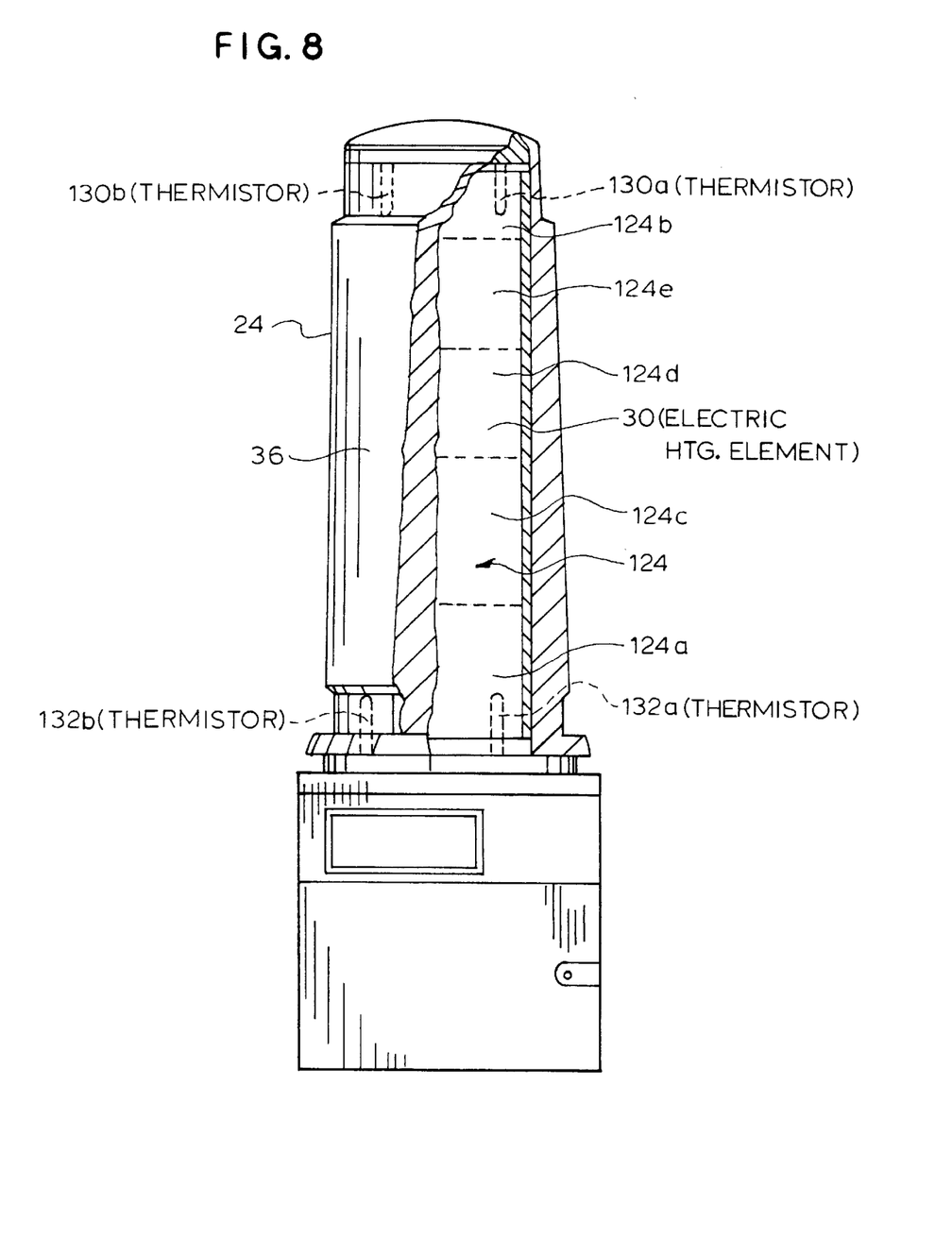
FIG. 8 is a side sectional view with parts broken away of the heater of FIG. 1 with the attachable assembly shown in FIG. 7 removed.

Referring to FIGS. 2, 7 and 8, during operation, the fluid to be warmed flows through the inlet tube 104 and into the cuff 44 and upward along the heated mandrel 24. Because the fluid will be coldest at the lower portion 46a of the passageway 46 and the potential for overheating the fluid greatest adjacent the outlet 78, it is preferred that the heater 26 be configured to produce a heat output which varies and decreases along the length of the mandrel 24. Referring to FIG. 2, in the preferred embodiment, the heating sheet 26 is constructed so that the heat output of the heating sheet 26 is divided into five lateral bands 124. Each band is of uniform heat output density, and the bands differ from each other in heat output density by a desired ratio. The lower lateral band 124a disposed along the lower end of the core 16 has a greater output than the upper lateral band 124b at the upper end with the intermediate bands 124c–124e of an increasing heat output.

The heating sheet 26 may be configured with the heat output density of the upper band 124b approximately 20% of the heat output density of the lower band 124a. It has been found that forming the lower intermediate band 124c with a heat output density about 75% of the lower band, the intermediate band 124d with a heat output density about 50% of the lower band 124a and the intermediate band 124e with a heat output density of about 30% of the lower band produces good results. It is also anticipated that providing the heating core 16 with other distributions of heat outputs may also produce satisfactory results.

Referring FIG. 8, to sense the temperature of the fluid so that the heating of the fluid can be controlled, the apparatus 10 includes at least one and preferably a plurality of temperature sensing devices 130 disposed in close proximity to the upper end of the mandrel 24. Also the apparatus 10 includes at least one and a plurality of temperature sensing devices 132 disposed in close proximity to the lower end of the mandrel 24. Preferably the devices 130 and 132 are disposed in the respective ends of the mandrel 24. To provide good temperature sensing coverage and a safety feature, both the upper and lower sensing devices 130, 132 preferably include two (2) individual temperature sensing devices, with each of the devices in the pair disposed at opposite sides of the mandrel 24 or 180° apart. It is also preferred that the lower devices 132 are vertically aligned the upper devices 130. To provide a safe and reliable system, the temperature sensing devices 130 and 132 are thermistors. Other types of temperature sensing devices may also be employed.

The Control System

Figure 4:
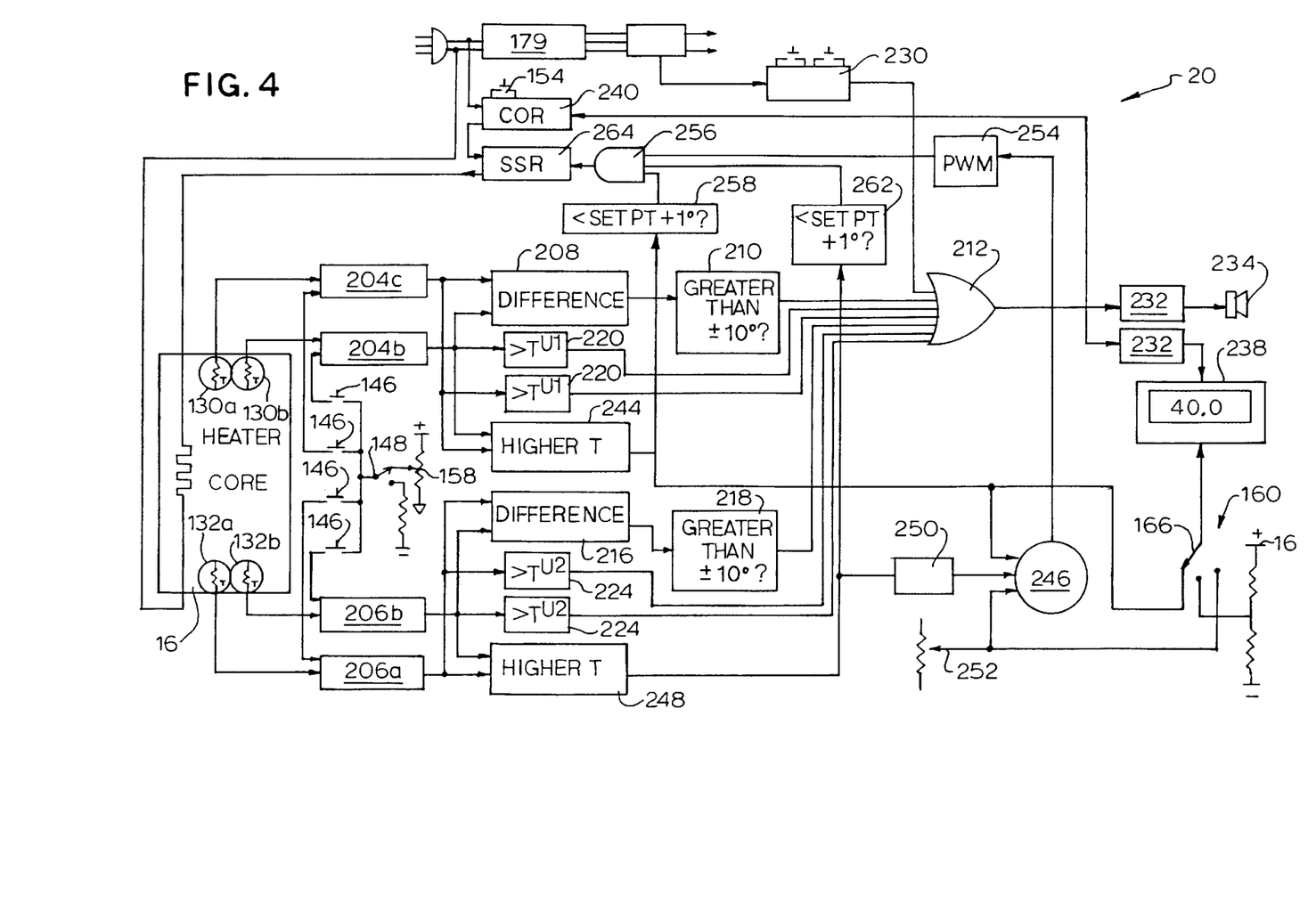
FIG. 4 is a functional block diagram of the electrical system forming a part of the apparatus of FIG. 1.

Referring to FIG. 4, the control system 20 is particularly suited to control the operation of the heater core 16 to safely heat the fluid, as the fluid flows through the disposable assembly 14 (FIG. 1) under widely varying flow rate, to a desired temperature without overheating. Typical, inputs to the system 20 are the signal outputs from the upper temperature sensing devices 130a and 130b and the lower temperature sensing devices 132a and 132b. The signal outputs of upper temperature sensing devices 130a and 130b are amplified by circuits 204a and 204b respectively. Similarly the signal outputs of lower temperature sensing devices 132a and 132b are amplified by circuits 206a and 206b.

To verify that both of the upper temperature sensing devices 130a and 130b are functioning properly, one of an amplified output from each of the upper sensing devices is provided to a first comparator circuit 208. The circuit 208 determines the difference in the two temperatures being sensed by the sensing devices 130a and 130b. The difference is then compared to a predetermined alarm value $\Delta T^1$, preferably 10° C., by a circuit 210. If the difference in the two temperatures being sensed by the sensing devices 130a and 130b is at least equal to or greater than $\Delta T^1$, a likely malfunctioning upper temperature sensing device 130a , 130b is indicated and a first alarm signal is output to OR switch 212.

To verify that both of the lower temperature sensing devices is 132a and 132b are functioning properly, one of an amplified output from each of the lower sensing devices 132a and 132b is provided to a second comparator circuit 216. The circuit 216 determines the difference in the two temperatures being sensed by the sensing devices 132a and 132b. The difference is then compared to a predetermined alarm value $\Delta T^2$, preferably 10°, by a circuit 218. If the difference in the two temperatures being sensed by the sensing devices 132a and 132b is at least equal to or greater than ΔT², a likely malfunctioning lower temperature sensing device 132a or 132b is indicated and a second alarm signal is output to OR switch 212.

Referring briefly to FIG. 1, to signal any overheating of the fluid as the fluid flows through the cup 14 (FIG. 1), the control system 20 monitors the temperature of the mandrel 24 and alarms and shuts off the power to the heating core 16 when a predetermined upper limit temperature $T^{U1}$ is at least equaled or exceeded. In particular, a second amplified output from each of the upper sensing devices 130a and 130b is provided to individual corresponding third comparator circuits 220. Each of the third comparator circuits 220 compares the sensed input temperature to upper temperature limit $T^{U1}$. Should one of the third comparator circuits 220 determine that the sensed input temperature is greater than the upper alarm temp $T^{U1}$, a third alarm signal from that circuit is outputted to OR switch 212. When the fluid being warmed is blood or the like, $T^{U1}$ is preferably 42°.

Similarly, second amplified outputs from each of the lower sensing devices 132a and 132b are provided to corresponding individual fourth comparator circuits 224 which compare the input signal to a predetermined alarm temperature $T^{U2}$. $T^{U2}$ preferably equals $T^{U1}$. If one of the circuits 224 determines that the higher temperature being sensed is at least equal to or higher than $T^{U2}$, that circuit outputs a fourth alarm signal to OR switch 212.

Thus, it can be seen that the control system 20 uses the indicated temperatures provided by the temperature sensing devices to determine whether one of the upper sensing devices 130a and 130b is operating improperly and whether one of the lower sensing devices 132a and 132b is operating improperly, and produces an alarm signal if determination is made that a sensing device is not operating properly. Also the control system 20 determines whether any one of the upper sensing devices 130a and 130b or any one of the lower sensing devices 132a and 132b is sensing a temperature at least equal to or greater than the respective predetermined alarm temperatures, and producing an alarm signal if the alarm temperatures are equaled or exceeded.

The control system 20 also includes a voltage monitoring circuit 230 which monitors the electrical power being provided to the heating sheet 26 and the components making up the control system. The voltage monitor 230 outputs a fifth alarm signal to the OR switch 212 if a fault condition is determined.

If the OR switch 212 receives the first, second, third, fourth or fifth alarm signal from circuit 210, circuit 218, circuits 220, circuits 224 or circuits 230, respectively, a signal is transmitted to alarm circuits 232. One of the alarm circuits 232 activates at least one audible alarm 234 which alerts health care providers to a fault condition. A second alarm circuit 232 may actuate a visual alarm provided by an action such as blinking the backlight or numerals of a display panel 238. In addition to activating the alarm 234, the output form the OR switch 212 may also be sent to activate a cut off relay 240 which switches off the power being supplied to the heating sheet 26 (FIG. 2) at the heater core 16. In the preferred embodiment, the cut off relay 240 may be switched back on when the alarm condition is no longer present, by turning the unit off and on.

Referring also to FIG. 1, the control system 20 operatively controls the heating of the fluid in at least partial dependence on the temperatures sensed by at least one of the upper temperature sensing devices 130a and 130b and the lower temperature sensing devices 132a and 132b. The temperature of the fluid when the fluid flows from the apparatus 10 is typically highest when the fluid is adjacent to the upper end 70 of the mandrel 24. Therefore, in the preferred embodiment, the control system 20 controls the heating of the core 16 in at least partial dependence on the highest temperature sensed by the upper temperature sensing devices 130a and 130b. In this operational process, an amplified output from each of the upper temperature sensors 130a, 130b is supplied to a fifth comparator circuit 244. The fifth circuit 244 outputs the higher of the two temperature inputs to a first operational circuit 246. The operational circuit 246 compares the input temperature to a set point temperature $T^{SP}$ and averages the difference over a predetermined time period in determining the desired amount of power for the heater 26. The set point temperature input is provided by an adjustable set point circuit 252 which is set to the desired temperature $T^{SP}$ of the fluid exiting the apparatus 10. The setting of the desired temperature $T^{SP}$ is typically done during manufacture.

The output from the fifth circuit 244 is also sent to the display panel 236, to be displayed to the users of the apparatus 10.

The control system 20 is also preferably constructed to adjust the heat output of the heating unit 12 to compensate for sensed changes in the flow rate of the fluid through the apparatus 10. Such adjustment is beneficial if the heat output of the heating unit 12 is primarily controlled by the sensed temperature of the fluid about the upper end 70. For instance, the warming apparatus 10 may have achieved a steady state heat output and temperature control for a certain flow rate of fluid. Without any other control features, a sudden alteration in flow rate will not vary the heat output of the heating unit 12 until the upper sensors 130 detect a change in the temperature of the upper end 70.

For example, a sudden increase in the flow rate of blood while maintaining a constant supply of heat will cause the temperature of the blood leaving the apparatus 10 to decrease. As set forth below, the heat output of the unit 12 will likely then increase, but the increase will likely not be timely or sufficient to warm blood which is at or approaching the outlet of the cuff 44, to the desired temperature. Therefore, it is desirable to sense a changing flow rate as soon as possible, and in the preferred embodiment, at a location in close proximity to the inlet 74.

In the preferred embodiment, the changes in the flow rate may be detected by monitoring the change in the temperature of the mandrel 24 in close proximity to the lower end 76 of the passageway 46 where the fluid initially flows into the cuff 44. With the heating unit 12 providing a relatively constant heat output and the input fluid at lower temperature, substantial changes in the flow of the fluid will generally be reflected in changes in the temperature of the lower end of the mandrel 24 as sensed by the lower temperature sensing devices 132a and 132b. For example, a substantial increase in the flow of fluid into the passageway 46 will generally cause the lower end of the mandrel to cool off fairly rapidly. Thus, the heat output of the heater core 16 should be increased. Conversely, a substantial decrease in the flow of fluid into the passageway 46 will generally cause the lower end of the mandrel 24 to heat up fairly rapidly. Thus, the heat output of the heater core 16 should be decreased.

An output from each of the lower temperature sensors amplifying circuits 224 is provided to a sixth comparator circuit 248. The output from the sixth comparator circuit 248 represents the higher temperature being sensed by the lower temperature sensing devices 132a and 132b, and is provided to a differential circuit 250 which generates the second input to the operational comparator circuit 246. The second input generated by the differential circuit 250 varies at least in partial dependence on the rate of change in the temperatures being sensed by the lower temperature sensing devices 132a and 132b.

The operational circuit 246 sums the inputs from the differential circuit 250 and the power determination based on the average difference between the sensed temperature and the Set Point Temperature $T^{SP}$ and outputs a signal to a power adjusting circuit 254. Preferably the power adjusting circuit 254 is a pulse width modulator or the like, although other appropriate adjusting circuits are also contemplated. The output from the power adjusting circuit 254 is provided as a first input to junction 256.

The control system 20 also includes a safety feature chiefly directed to prevent overheating of fluid leaving the apparatus 10 and the resulting activation of the alarm circuit 232. The safety feature includes the process of shutting off the power to the heating core 16, when any one of the upper temperature sensing devices 130a and 130b and lower temperature sensing devices 132a and 132b senses a trigger temperature $T^T$. The trigger temperature is preferably between the set point temperature $T^{SP}$ and alarm temperatures $T^{U1}$ and $T^{U2}$. In the preferred embodiment the trigger temperature $T^T$ is set by the control system 20 to be equal to the set point temperature $T^{SP}$ plus 1° C. The power is restored when the sensed temperature falls below the trigger temperature $T^T$. An output from the third comparator circuit 244 of the higher of the temperatures sensed by the upper temperature sensing devices 130a and 130b, is provided to a first set point comparator circuit 258 which compares the temperature to the trigger temperature $T^T$. If the temperature at least equals or exceeds the trigger temperature $T^T$, an indicative output is provided as a second input to the junction 256.

Similarly, an output from the sixth comparator circuit 248, which indicates the higher of the temperatures sensed by the lower temperature sensing devices 132a and 132b, is provided to a second set point comparator circuit 262 which compares the temperature to a second trigger temperature $T^{T2}$, which is preferably the same as the first trigger temperature (although it is contemplated that the trigger temperatures may vary). If the indicated temperature at least equals or exceeds the second trigger temperature, an indicative output is provided as a third input to the junction 256.

Unless the junction 256 receives the output from the first set point comparator circuit 258 or the output from the second set point indicator circuit 262, the junction 254 transmits the first input, supplied by the power adjusting circuit 254, onward to a switching circuit 264, preferably a zero crossing solid state relay or the like. The switching circuit 264 selectively controls the power being provided to the heater 26, so that sufficient heat is being outputted by the heater to warm the fluid flowing through the apparatus, to the desired exit or set point temperature.

However, an output from either of the set point comparator circuits 258, 262 overrides the output from the power adjusting output 254 to cause the switching circuit 264 to shut off power to the heater 26. The control of the power adjusting circuit 254 is restored when the highest sensed temperature falls below both of the trigger temperatures $T^{T1}$, $T^{T2}$.

Although in the preferred embodiment, the control logic of the warmer 10 is achieved by using a novel arrangement of circuit elements, other methods of controlling the heater 26 output to controllably heat fluid are also contemplated. It is envisioned that control may also be achieved by using a microprocessor and appropriate programming. Such programming may be placed in volatile or nonvolatile memory or combinations of multiple types of memory. In addition portions of the program may be contained in different memory units some of which may be removable to allow remote programming or easy configuration of the operating characteristics of the warmer 10 for different fluids.

The Control Panel

Figure 5:
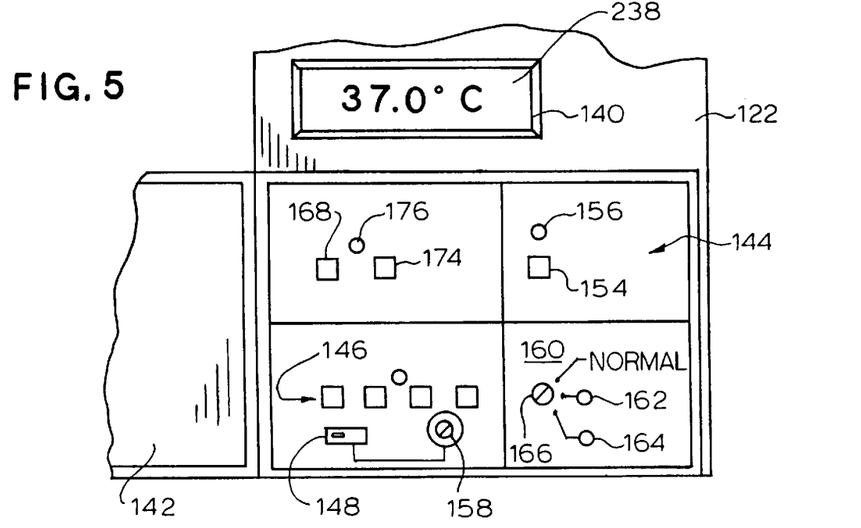
FIG. 5 is a front elevational view of a control panel of the fluid warming apparatus of FIG. 1.

Referring to FIGS. 1 and 2, the base 18 is formed in a general configuration of a cube. A forward face 122 of the base 18 forms a viewing opening 140 through which the display 238 is visible. Forming a part of the base 18 and attached to the forward face 140 by a hinge, is a latch door 142. Referring to FIG. 5 in conjunction with FIG. 4, the latch door 142 provides a protective covering to a control panel generally indicated at 144. The control panel 144 provides a simplified means for the technician to conduct tests on the control system 20 of the apparatus 10. Included in the control panel are button switches 146 which form a test for the upper temperature sensors 130a and 130b and the lower temperature sensors 132a and 132b. Affiliated with the button switches 146 is a switch 148 for selectively choosing one of a plurality of test conditions. Pressing of one of the button switches 146 creates a simulated fault condition in the respective temperature-sensing device and results in tripping the alarm circuit 232 or an alarm condition. In addition, a light 150 illuminates to indicate when a button switch 146 has been depressed.

The specific test condition is dependent on the position of the switch 148. In a first position, pressing one of the button switches 146 simulates a failed sensor, thereby causing the alarm circuit 232 to activate, activating the cut off relay 240. The cut off relay 240 may be reset by a reset switch 154. When the reset switch 154 is depressed an associated LED indicator light 156 is illuminated, the relay 240 is reset and the indicator light 150 is extinguished.

By setting the switch 148 in a second position and depressing one of the switches 146, an over temperature condition may be simulated using a potentiometer 158. As the potentiometer is adjusted, the technician may view the display 238, and if the control system 20 is working properly, the alarm circuit 232 activates when the alarm temperature, as shown in the display, is exceeded. The cut off relay is activated and the indicator light 150 also lights. Pressing the reset switch 154 resets the circuitry.

In addition, the control system 20 includes means 160 for determining whether the display 238 is properly calibrated. More particularly, the means for verifying the calibration of the display 238 is a predetermined reference voltage circuit 161 with an associated light 162. The temperature set point calibration means also includes the adjustable set point circuit 152 and an associated light 164.

To set the warming apparatus 10 in the proper mode for either normal operation; display calibration, or temperature set-point adjustment, a three position rotary switch 166 is preferably used. To perform one of the tests, the mode selector switch 166 is rotated to the proper position and the technician looks at the temperature shown in the display. The light 162 or 164 will illuminate to also indicate which test is being run. If the display calibration test is being run the display should indicate a temperature corresponding to the predetermined test voltage. For example, the test voltage may correspond to 50° C., therefore, the display, if properly functioning, should show that temperature. If the set point test is being run, the display should indicate the temperature of the set point. The third position of the switch 166 is to place the heating unit 12 in normal operation, and both of the indicator lights 152, 154 are no longer illuminated.

The control panel 144 also includes a switch 168 and associated for testing the control circuitry and a switch 174 for testing the circuitry which adjusts the heat output i dependence on the rate of change of the lower sensors light 170. Depressing either of these switches 168, 174, also illuminates a corresponding light 176, activates the alarm circuit 232 and shuts off the cut off relay 240. The alarm 232 and cut off relay 240 may be reset and the illuminated light 176 extinguished by pressing the reset switch 154.

In summary, various alarm conditions and the visual display may be checked by a technician through utilizing test switches. In performing each test, the corresponding indicating light is illuminated. Thus, when all the tests are completed and the circuitry appropriately reset, all the lights will be out.

After the testing is completed, the door 142 is closed and locked to prevent access by later users of the apparatus 10. To help insure the proper operation of the apparatus 10, the later user is limited to an on off switch 179 (FIG. 1). Should a "nuisance" alarm condition occur in later use, the control system 20 may be reset by turning the apparatus 10 off and back on with the on-off switch 179. Continued alarm indications after such a maneuver will likely indicate a malfunctioning apparatus 10.

Referring back to FIG. 1, the preferred embodiment of the base 18 also includes a friction-fit holder 180 for retaining a bubble trap(not shown) which is commonly used while administering blood or the like to a patient. The apparatus 10 also includes a cover 182 which fits about a top end of the heating core 16 for environmental protection.

For mounting, the apparatus 10 includes a clamp 184, attached to the base 18, which clamps the apparatus to a rod 186. The clamp 180 also allows the apparatus 10 to be easily removed from the rod 186. The rod 186 is usually found in a vertical orientation, but due to the apparatus's 10 operating characteristics, the apparatus may be operated in any orientation.

In operation, the assembly 14 is slidably inserted over the mandrel 24 until the standoffs 60 contact the exterior surface 36 of the mandrel 24. The contact between the standoffs 60 and exterior surface 36 center the restraint 40 relative to the surface 36, establishing the passageway 46 with the uniform gap or thickness 48 (FIG. 2) between the restraint and surface over the majority of surface area of the surface 36. Also, the wider spacing between the restraint 40 and mandrel 24 at the lower radial groove 94 and the upper groove 100 form the boundary 86a of the inlet manifold portion 86 and the boundary 98a of the outlet manifold portion 98 of he passageway, respectively.

The lower apron 108 of the restraint 40 contacts the boss 110 on the mandrel 24. The assembly 14 may then be rotated relative to the heating unit 12 until the ear 118 snaps under the notch 120 (FIG. 1a) formed in the clamp 116.

Fluid then flows into the cuff 44 by flowing through the inlet tube 104. The tube 104 directs the fluid so that when the fluid enters the cuff 44, the fluid is directed tangentially relative to the surface 36 of the mandrel 24 and also along the length of the manifold 86. As the fluid flows into the passageway 46, air is purged from the passageway, priming the apparatus 10.

As fluid first enters the passageway 46, the fluid fills the inlet manifold 86 circumscribing the mandrel 24. The fluid then flows along the length of the mandrel 24 in a sheet-like flow. The fluid is then heated as the fluid flows in a generally unidirectional unrestricted vertical flow upward about the heater core 16. When the apparatus 10 is activated, the control system 20 (FIG. 4) controls the heat input into the flowing fluid so that the fluid is warmed to a desired temperature before the fluid flows from the passageway 46.

The pressure of the fluid forms an inward radial force pressing the inner sidewall 57 of the side sheets 54 against the mandrel 24 and a counteracting outward radial force to press the outer sidewall 57 of the sheets 54 against the restraint 40. The outward force is evenly distributed about the circumference of the restraint 40, to promote the centering of the restraint on the mandrel 24, and the gap 48 and passageway 46 are of generally constant thickness about the heating core 16. The constant thickness of the passageway 46 promotes even heating of the fluid to prevent hot spots. Also, the pressing of the inner of the side sheets 54 against the heater core 16 facilitates heat transfer to the fluid.

The heated fluid is then collected in the outlet manifold 98 and exits the manifold via the outlet tube 105 in a direction aligned with the length of the manifold and generally tangential to the surface 36 of the mandrel 24.

If the upper tube 80 is connected to an administration set which includes a bubble trap (not shown), the bubble trap can be attached to the clamp 180.

After the medical procedure has reached a point where warmed blood is no longer needed, the heating unit 12 is shut off, and the assembly 14 is then rotated relative to the heating unit 12 until the ear 118 snaps out from under the notch 120 formed in the clamp 116. The assembly 14 may then be slidably removed in an upward direction from the mandrel 24, and disposed of in the proper manner.

As can be seen from the above operational description, the set up and operation of the warming apparatus 10 is fairly simple and the amount of operational supervision is low. In general terms, the set up includes a sliding snap fit of the disposable assembly 14 onto the heating unit 12. Depressing the on off switch 179 activates the assembly 10. Supervision includes observing for alarms and monitoring the displayed temperature.

While a particular embodiment of the blood warming apparatus has been shown and described, it will be appreciated by those skilled in the art that changes and modifications may be made thereto without departing from the invention in its broader aspects and as set forth in the following claims.

What is claimed is:

1. An apparatus for warming a flow of parenteral fluid through an assembly, the assembly having an inlet and an outlet and forming a passageway for the flow of parenteral fluid through the assembly, the apparatus comprising:

a general elongated mandrel having an exterior surface formed of a material having a high thermal conductivity and shaped to slidingly receive the assembly so that the assembly envelops the surface along at least a portion of the length of the mandrel:

a selectively controlled heater in conductive contact with the surface, a control circuit operably connected to the heater and including at least one first temperature sensor to sense a temperature of the mandrel at a location on the surface in close proximity to the inlet of the assembly when the assembly is placed about the mandrel and means for adjusting heat output of the heater in dependence at least in part on a rate of change of temperature sensed by the first temperature sensor.

2. The apparatus of claim 1 wherein the control system further includes at least one second sensor to sense a temperature of the mandrel at a location in close proximity to an outlet of the assembly and means for adjusting the heat output based at least in part on the temperature sensed by the second sensor.

3. The apparatus of claim 2 wherein the control systems includes a plurality of second sensors and means to compare the difference in temperatures being sensed by the second temperature sensors with a predetermined value.

4. The apparatus of claim 1 wherein the control system includes a plurality of first temperature sensors, and means to compare the difference in temperatures being sensed by the first temperature sensors with a predetermined value.

5. An apparatus for warming a flow of parenteral fluid through an assembly, the assembly having an inlet and an outlet and forming a passageway for the flow of patenteral fluid through the assembly, the apparatus comprising:

a general elongated mandrel having an exterior surface formed of a material having a high thermal conductivity and shaped to slidingly receive the assembly so that the assembly envelops the surface along at least a portion of the length of the mandrel;

a selectively controlled heater in conductive contact with the surface; and a control circuit operably connected the heater and including at least one first temperature sensor to sense the temperature at a location on the surface and a means for varying the heater output based at least in part on the temperature sensed by the first temperature sensor, said varying means including first means for varying the heat output to obtain a desired temperature in at least partial dependence on the sensed temperature, and second means for shutting off power to the heater when the sensed temperature is at least one of equal to or greater than an upper limit temperature.

6. An apparatus for warming a flow of fluid comprising:

an assembly shaped generally frusto-conical and defining a longitudinal axis, the assembly forming an inlet and outlet and a sealed passageway for the fluid from the inlet to the outlet, the inlet being proximate one end of the assembly and the outlet being proximate the other end of the assembly, the assembly including an exterior restraint defining an outer boundary of the passageway;

a general elongated heated mandrel defining a longitudinal axis, the mandrel having an exterior surface with at least a portion formed of a material having a high thermal conductivity and shaped to slidingly receive the assembly so that the assembly envelops the exterior surface along at least a portion of the length of the mandrel, the exterior surface defining an inner boundary of the passageway, the assembly and the exterior surface of the mandrel being configured to form the passageway with a generally constant thickness over at least a portion of the length of the passageway when the assembly is disposed in a desired position relative to the mandrel.

7. The apparatus of claim 6 wherein the assembly includes a flexible sidewall forming an interior wall for the passageway.

8. The apparatus of claim 7 wherein the assembly includes a bag sealingly forming the passageway.

9. The apparatus of claim 6 wherein the assembly is configured to engage the mandrel and dispose the assembly in the desired relative position.

10. The apparatus of claim 9 where in the assembly includes means attached to the restraint for engaging the mandrel and establishing the desired relative position.

11. The apparatus of claim 6 wherein at least one of the restraint and the mandrel are configured to form an inlet manifold portion and a second portion of the passageway, the inlet manifold having a thickness greater than the thickness of the second portion, the second portion extending a majority of the length of the passageway along the mandrel.

12. The apparatus of claim 11 wherein the inlet manifold is configured to extend circumferentially about the mandrel.

13. The apparatus of claim 11 wherein the mandrel includes a radial groove defining the inlet manifold.

14. The apparatus of claim 11 wherein the assembly is configured to direct an inlet flow of fluid along the inlet manifold.

15. The apparatus of claim 11 wherein the assembly includes means for directing an inlet flow of blood along the inlet manifold.

16. The apparatus of claim 6 wherein the restraint and mandrel are configured to form the passageway with a generally uniform thickness over the majority of the length of the passageway.

17. The apparatus of claim 6 wherein the internal surface of the restraint is frustro/conically shaped and free of shapes which may pinch the passageway over a majority of the length of the passageway.

18. The apparatus of claim 11 wherein the assembly is configured to direct an inflow of blood out into the inlet manifold in a direction tangential to the exterior surface of the mandrel and generally normal relative to a longitudinal axis defined by the mandrel.

19. The apparatus of claim 6 wherein at least one of the restraint and the mandrel are configured to form an outlet manifold portion of the passageway, the outlet manifold having a thickness greater than the thickness of a portion of the passageway extending over a majority of the length of the passageway along the mandrel.

20. The apparatus of claim 19 wherein the outlet manifold is configured to extend circumferentially about the mandrel in close proximity to an end of the mandrel.

21. The apparatus of claim 19 wherein the mandrel includes a radial groove defining a portion of the outlet manifold.

22. The apparatus of claim 19 wherein the assembly is configured to direct an outlet flow of fluid from the passageway in a direction generally aligned with the outlet manifold.

23. The apparatus of claim 19 wherein the assembly is configured to direct an outflow of blood out of the inlet manifold in a direction tangential to the exterior of the mandrel and generally normal relative to a longitudinal axis defined by the mandrel.

24. A process for adjusting the heat output of a parenteral fluid warming heater having a heating mandrel and an assembly disposed about the mandrel, the assembly providing a sealed passageway for a flow of a parenteral fluid through the heater, the process being characterized by the fact that it comprises the steps of:

choosing a target temperature;

measuring a first temperature at a first location on the mandrel;

measuring a second temperature at a second location on the mandrel; and adjusting a heat output of the mandrel in dependence on both a difference between the target temperature and the first temperature and a rate of change of the second temperature.

25. The process of claim 24 wherein the adjusting includes varying power supplied to a electric heating element in heat conductive contact with the mandrel and further including the steps of choosing an upper temperature limit greater than the target temperature;

comparing at least one of the first temperature and the second temperature to the upper temperature limit; and switching off the power to the heating element when the at least one of the first temperature and the second temperature is at least one of equal to and greater than the upper temperature limit.

26. The process of claim 25 further including the steps of choosing an alarm temperature;

comparing at least one of the first temperature and the second temperature with the alarm temperature; and generating an alarm when the at least one of the first temperature and the second temperature is at least one of equal to and greater than the alarm temperature.

27. The process of claim 25 further including:

measuring a third temperature at a third location on the mandrel;

comparing the third temperature with at least one of the first temperature and the second temperature; and generating an alarm signal when a difference between the third temperature and the compared temperature is at least one of equal to and greater than a predetermined temperature differential.

28. An apparatus for warming a flow of fluid comprising:

an assembly shaped generally frustum-conical and defining a longitudinal axis, the assembly forming an inlet and outlet and a sealed passageway for the fluid from the inlet to the outlet, the inlet being proximate one end of the assembly and the outlet being proximate the other end of the assembly, the assembly including an exterior restraint defining an outer boundary of the passageway;

a general elongated heated mandrel defining a longitudinal axis, the mandrel having an exterior surface with at least a portion formed of a material having a high thermal conductivity and shaped to slidingly receive the assembly so that the assembly envelops the exterior surface along at least a portion of the length of the mandrel, the assembly and the exterior surface of the mandrel being configured to form the passageway so that as fluid flows through the passageway the fluid flow forms a generally uninterrupted sheet like flow over a majority of the surface area of the mandrel when the assembly is disposed in a desired position relative to the mandrel.

29. An apparatus for warming a flow of fluid through an assembly shaped generally frustum-conical and defining a longitudinal axis, the assembly forming an inlet and outlet and a sealed passageway for the fluid from the inlet to the outlet, the inlet being proximate one end of the assembly and the outlet being proximate the other end of the assembly, the assembly including an exterior restraint defining an outer boundary of the passageway, the apparatus comprising:

a general elongated heated mandrel defining a longitudinal axis, the mandrel having an exterior surface with at least a portion formed of a material having a high thermal conductivity and shaped to slidingly receive the assembly so that the assembly envelops the exterior surface along at least a portion of the length of the mandrel, the mandrel forming a hollow interior cavity; and a electrical sheet heater disposed within the cavity and in conductive contact with the mandrel, the heater formed with a plurality of bands of differing heat output along the length of the mandrel.

30. The apparatus of claim 29 wherein the heat output of a first band of the bands is greater than a second band of the bands, the first band being disposed in close proximity to the inlet of the assembly when the assembly is slidingly disposed about the mandrel.

* * * * *